United States Patent [19]
McNulty et al.

[11] Patent Number: 6,119,026
[45] Date of Patent: Sep. 12, 2000

[54] RADIATION APPARATUS AND METHOD FOR ANALYSIS OF ANALYTES IN SAMPLE

[75] Inventors: Chris McNulty, Garland, Tex.; Ganapati Ramnath Mauze, Sunnyvale, Calif.

[73] Assignee: Hewlett-Packard Company, Palo Alto, Calif.

[21] Appl. No.: 09/031,369

[22] Filed: Feb. 26, 1998

Related U.S. Application Data

[60] Provisional application No. 60/067,698, Dec. 4, 1997.
[51] Int. Cl.⁷ .................................................. A61B 5/00
[52] U.S. Cl. ............................................ 600/310; 600/316
[58] Field of Search ................................. 600/310, 316, 600/322, 323, 326, 473, 476

[56] References Cited

U.S. PATENT DOCUMENTS 5,490,505  2/1996  Diab et al. ............................... 600/323
5,575,284  11/1996  Athan et al. ............................. 600/323

*Primary Examiner*—Eric F. Winakur

[57] ABSTRACT

A technique that uses wavelet analysis to analyze the concentration of an analyte in a sample. The technique includes irradiating the sample with electromagnetic radiation and detecting a resulting radiation from the sample to obtain spectral data. The electromagnetic radiation irradiated on the sample results in radiation interaction, such as reflection, scattering, and transmission, from the sample. The radiation interaction results in a resultant electromagnetic radiation from the sample, such as reflected radiation, scattered radiation, or transmitted radiation. The resultant electromagnetic radiation includes signals indicative of the analyte. The spectral data is digitally processed using wavelet analysis to increase proportionally the signal indicative of the analyte in the data. A modeling algorithm is applied to the processed data to determine the quantitative characteristics of the analyte in the sample.

20 Claims, 12 Drawing Sheets

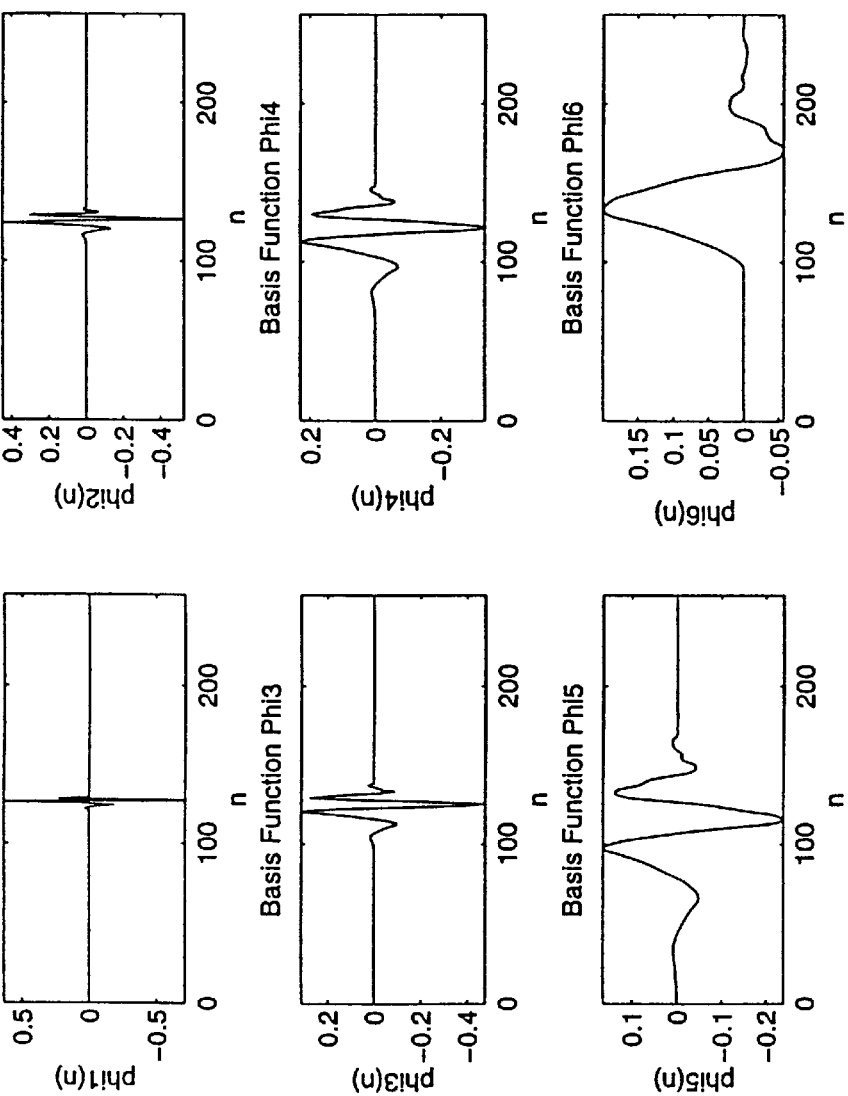

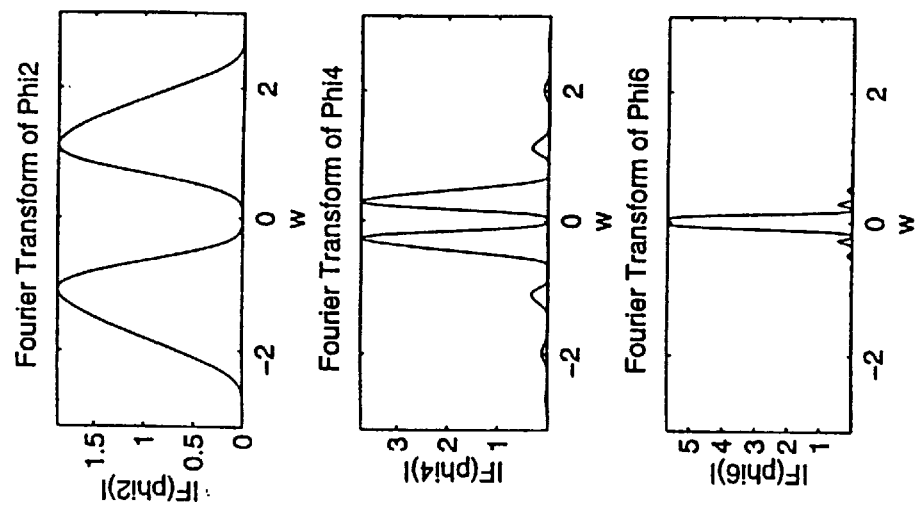
Fig. 2A  Fig. 2B  Fig. 2C  Fig. 2D
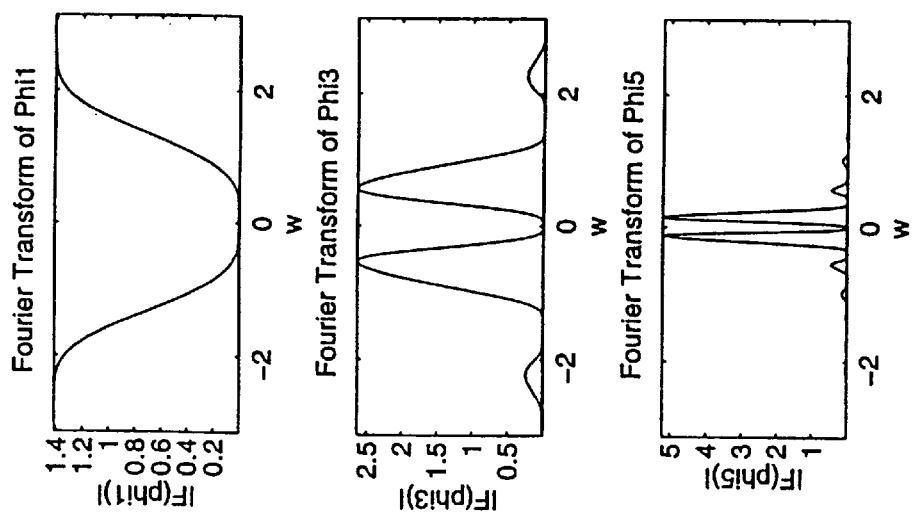
Fig. 2E  Fig. 2F
Fig. 2

RADIATION APPARATUS AND METHOD FOR ANALYSIS OF ANALYTES IN SAMPLE

This application claims benefit of Provisional Application Ser. No. 60/067,698 filed Dec. 4, 1997.

FIELD OF THE INVENTION

The present invention relates to techniques for analyzing chemicals in a sample using radiation, and more particularly to techniques for non-invasively analyzing chemicals in human blood using radiation.

BACKGROUND

The analysis of blood components is an important diagnostic tool for better understanding the physical condition of a patient. Presently, adequate noninvasive blood analysis technology is not currently available and blood samples still need to be obtained by invasive methods from a great number of patients every day for analysis. A well known example of such needs is the monitoring of glucose levels by a diabetic individual. Similarly, concentration of other physiological chemicals are important for determining the health condition of some individuals.

Research effort has been directed to non-invasive analysis of blood chemicals. Take the example of glucose. Glucose has several absorption peaks in the near infrared and the far infrared. Researchers have made progress in measuring glucose in solution by means of absorption of such radiation. Unfortunately, water, which is a major component of tissue and blood also, absorbs heavily in most of these regions. This makes it almost impossible to extract glucose information by absorption in most of these regions. However, in the near infrared some weak absorption bands of glucose overlap valleys in the water absorption bands. These bands, being weak absorption bands in the vicinity of huge water bands, are extremely difficult to analyze, particularly in complex systems such as tissue where several other analytes are also present and are themselves fluctuating. Successful glucose analysis therefore requires separating a weak signal in the midst of influences of chemical interference and temperature and flow related fluctuations.

Several techniques for processing the spectral data to eliminate these influences have been developed. Multivariate regression analysis such as PLS (partial least square) methods and PCR (principal component resolution) methods have been widely applied. More recently, Fourier filtering of the spectral data followed by multivariate regression analysis have been used to improve the prediction of glucose in biological samples. However, we have found that when the temperature of even simple aqueous samples varies over the human body temperature range, the predictive ability of these methods can be seriously reduced. Further, such prior techniques may not be robust enough to determine accurately the glucose composition when some of the interfering species such as proteins in the sample fluctuate over the normal range for human blood. Therefore, a better method of analyzing such data is required.

SUMMARY

In one aspect, the present invention involves a technique that uses wavelet analysis to determine the concentration of one or more analytes (e.g., a chemical such as glucose) in a sample. In an embodiment, the technique includes irradiating electromagnetic radiation on the sample, detecting a resulting radiation from the sample to obtain spectral data, digitally processing the data using wavelet-basis-function to increase proportionally the signal indicative of the analyte in the data, and applying a modeling algorithm to the digitally processed data to determine the quantitative characteristics of the analyte in the sample. The electromagnetic radiation irradiated on the sample interacts with the sample. The interaction results in a resultant electromagnetic radiation from the sample, such as reflected radiation, scattered radiation, or transmitted radiation. The resultant electromagnetic radiation includes signals indicative of the analyte. Therefore, by detecting and analyzing the resultant electromagnetic radiation, quantitative information on the analyte in the sample can be obtained. The resultant electromagnetic radiation spectra derived from the radiation interaction of the sample over the wavelength or frequency range or ranges include one or more bands whose magnitude or other characteristics are function of the concentration of the analyte of interest. The spectral information is then processed using wavelet analysis technique as described below. The present invention can be used, for example, to non-invasively measure the composition of one or more analytes (e.g. glucose concentration, lipid profile) of a sample, such as in-situ tissue or a blood sample, using spectral data obtained by the interaction of the radiation with the sample.

One of the steps in the implementation of this invention is the selection of a wavelet basis that is appropriate for the specific analysis. The wavelets in the basis are by definition functions that meet certain mathematical criteria (for general information about wavelets, see, Wavelets and Filter Banks, by Gilbert Strang and Truong Nguyen, Wellesley-Cambridge Press, 1996 ISBN: 0-9614088-7-1).

Although one can choose from a large collection of such functions, in analyzing the spectral information such as acquired in tissue spectroscopy, it is possible to choose a function that closely resembles the spectral signature such as absorption peak of the analyte to be measured. For example, some basis functions of Daubechies D8 are shaped substantially like the absorption peaks of pure glucose in the 4000–5000 wavenumbers range. Thus Daubechies D8 is one appropriate basis for implementing this invention.

In another embodiment of this invention a systematic optimization technique may be employed to test several sets of basis functions and choose one that best meets the chosen optimization criteria such as best correlation with the analyte signal or the least prediction error in a reference data set (a calibration set). Once the optimal set of basis functions has been determined, a mathematical prediction model is built using this set of basis functions. This prediction model can then be used to determine the concentration of the analyte of interest from a single data set such as an absorption spectrum obtained from an unknown sample.

BRIEF DESCRIPTION OF THE DRAWING

The following figures, which exemplify the embodiments of the present invention, are included to better illustrate the embodiments of the apparatus and use of the present invention. In these figures, like numerals represent like features in the several views.

FIG. 1A to FIG. 1F show examples of basis functions for a signal when using a ten-point Daubechies filter in discrete wavelet transform, DWT.

FIG. 2A to FIG. 2F show the corresponding Fourier Transform of the DWT basis functions of FIGS. 1A to FIG. 1F.

DETAILED DESCRIPTION OF THE INVENTION

Figure 3:
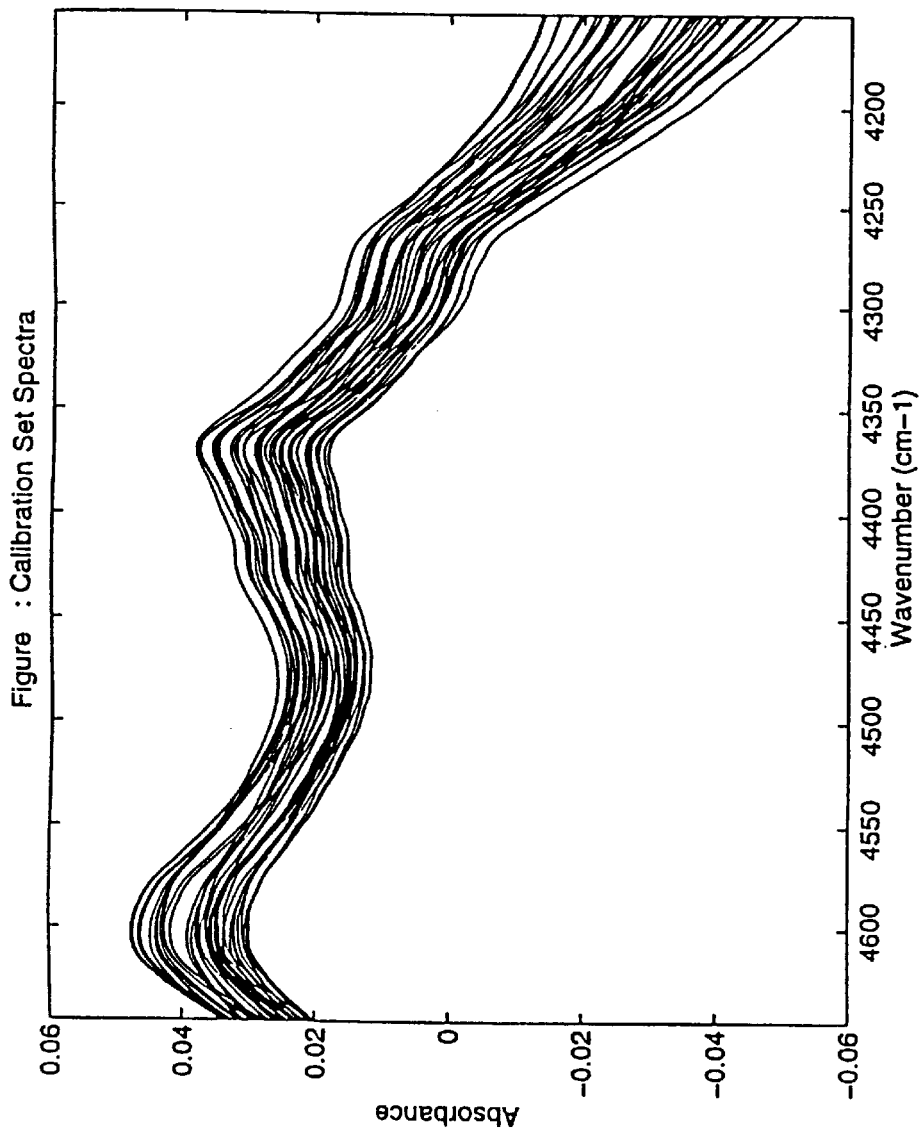
FIG. 3 shows an example of a calibration set of spectra.

In one aspect, the present invention provides a technique of non-invasively measuring quantitative information about one or more analytes (e.g., a chemical such as glucose) in a sample, e.g., a physiological liquid in a patient's body, using electromagnetic radiation by applying wavelet transform. As used herein, the term "sample" includes solid, liquid, and gas, and includes one that is contained in a container or a part of a whole, e.g., a part of a human hand. The technique of the present invention uses wavelet transform to analyze one or more analytes in the sample.

Wavelet Transform

Wavelet transforms, like Fourier transforms, can be considered as rotations of data in function space to a different domain. In the new domain the information content of the data can often be extracted with fewer and/or simpler mathematical treatments. For the Fourier transform the new domain is reached by projecting signals onto basis functions that are sine and cosine functions. For the wavelet transform it can be reached by projecting onto an infinite number of possible basis function sets called wavelets. These wavelet basis functions must meet certain mathematical criteria as described in Gilbert Strang and Truong Nguyen, supra (see also, Amara Graps, "An Introduction to Wavelets," IEEE Computational Science and Engineering, Summer 1995, Vol. 2, No, 2). They can be chosen from known sets or designed by the user to suit the particular application. Thus wavelet analysis provides access to information that can be obscured by methods that use fixed basis functions such as Fourier analysis.

The functions (vectors) in discrete wavelet transform (DWT), unlike those of discrete Fourier transform (DFT), are real, aperiodic, and non-zero over only a finite portion of the signal which is projected onto them. Although one skilled in the art will know the basis functions of different DWTs employing different filters, it is difficult to describe in limited space the basis functions in concise equations. The properties of the basis functions for DWTs can be better illustrated by graphs.

As an illustration, FIG. 1 shows six of the 256 basis functions ($\phi_i(j)$), where i represent the number of the different basis functions and j refers to the data points, for a 256-point signal when performing the D10 Daubechies DWT. The name of the DWT (D10 Daubechies) describes the type of basis functions used in the DWT. The Daubechies sets of basis functions are widely used in the implementation of DWTs. Detailed descriptions of how these and other wavelet basis functions are derived are given in Gilbert Strang and Truong Nguyen, supra, and should be obvious to those familiar with the art of wavelet analysis.

The basis functions of a DWT can be divided into different groups, called resolution levels. Each one of the basis functions plotted in FIG. 1 is an example of a basis function at a certain resolution level. The resolution level of $\phi_1(j)$ is numbered resolution level 7 since there are $2^7=128$ basis functions at this resolution level. In the lower levels of resolution levels, more data points are discarded than in the higher resolution levels. The only difference between any basis functions that are in the same resolution level is how much they are shifted. Thus, the other 127 basis functions in the same resolution level as $\phi_1(j)$ are all described by $\phi_1(j)=\phi_1(j-k)$, where k is the amount of shift. As a further example, in resolution level 6, there are 64 basis functions which are all shifted versions of $\phi2(j)$, since $2^6=64$. Resolution level 3, however, the lowest of the resolution levels in this wavelet transform, is slightly different than the rest of the resolution levels. For, the lowest resolution level of a DWT always has both a set of high-frequency basis functions and a set of low frequency basis functions. The eight high-frequency basis functions of resolution level 3 are all shifted versions of $\phi_5(j)$. The eight low-frequency basis functions of resolution level 3, on the other hand, are all shifted versions of $\phi_6(j)$.

The magnitudes of the Fourier transforms of the wavelet basis functions shown in FIG. 1 are displayed in FIG. 2. The basis functions in a resolution level all have exactly the same magnitude Fourier transforms. Thus, the plots in FIG. 2 would look no different for different basis functions in the same resolution level. From comparing FIGS. 1 and 2, one should be able to see that the "resolution" levels do not refer to "high-resolution" or "low-resolution". For, high resolution in the time-domain corresponds to low resolution in the frequency-domain, and high resolution in the frequency-domain corresponds to low resolution in the time-domain. Thus, the different resolution levels of the DWT can best be described as representing different levels of trade-off between time and frequency resolution.

According to the present invention, knowing what wavelets look like, one can go on to describe the method by which one uses the wavelet transform in order to predict the concentration of the analyte of interest (e.g., a chemical such as glucose). As an illustration, glucose is used below as an example to show the how the wavelet technique can be used. It is to be understood that one skilled in the art will be able to apply the present technique to other chemicals individually, e.g., alcohol, or as a group, e.g., lipids. To this end, for example, one can find a linear regression model for predicting glucose concentration ($y_{pred}$) from absorbance spectra ($x_n$), e.g., in the form of an equation ($y_{pred}=b_o+x'_1 b$) where $b_o$ and b are constants, and $x'_i$ represents spectra data. The equation will be described in detail below. In the present application, matrices are represented by bold, upper case letters; vectors are represented by bold, lower case letters; and scalars are represented by non-bold, lower case letters.

Establishing a Model

To implement a model of our invention, spectra are obtained from radiation interacting with a variety of samples containing known concentrations of the analyte of interest, i.e., glucose, as an example. Often, absorption is used for this purpose. However, since the employment of wavelet transform is applicable regardless of the form of electromagnetic wave interaction used, it is contemplated that other types of radiation interaction, such as transmission, reflectance, or light scattering can be used.

As an example, in the detection of glucose concentration in blood, near infra-red (NIR) radiation can be used to irradiate a body portion (e.g., the Thenar web, i.e., the webbing fold of skin between the thumb and index finger of person) and the light transmitted therethrough can be sensed to measure the light absorption. For glucose, a set of bands of absorption is in the ranges of 4000–5000 cm$^{-1}$ and 5800–6500 cm$^{-1}$. As stated earlier, an alternative is the transmittance of the light, which can be measured. Another alternative is to measure the reflectance of the irradiated light. In yet another alternative embodiment, radio frequency radiation can be used to irradiate the body portion to result in high frequency spectra (see, Fuller et al., WO 95/04496 for a description of apparatus and method for using radio frequency to estimate the concentration of a chemical in a liquid, said description is incorporated by reference herein). In each case, when the spectral signals are detected by appropriate detectors, they are converted into digital spectral data.

Since the analyte of interest has significant radiation interaction only in certain ranges, preferably, even before performing wavelet transforms to obtain wavelet basis functions, to reduce noise and reduce the amount of information to be processed, a certain amount of the spectral data in the time domain is truncated outside of these ranges before the spectral data is used to select the basis functions. Techniques for truncation of spectral data outside of a frequency range of interest are known to those skilled in the art. Thus, these spectra may be truncated so that they contain only those spectral regions known to have some correlation with analyte (e.g., glucose) concentration. For example, NIR glucose absorbance peaks would often be truncated to include only the glucose absorption ranges of 4000–5000 cm$^{-1}$ or 5800–6500 cm$^{-1}$ mentioned above.

In this invention, the spectral data obtained from a detector, or a truncated version thereof, is used to obtain a linear prediction model for the analyte of interest. While deriving this prediction model, we will refer to all absorbance spectra as spectra vectors ($x_n$). Practically, spectral data for deriving the prediction model will more conveniently be obtained from sample glucose solutions in containers. Using these spectra vectors, we will create a data matrix X, where each of the rows of X is one of the spectra vectors ($x_n$), as in Equation 1:

$$X = \begin{bmatrix} x'_1 \\ x'_2 \\ x'_3 \\ \vdots \\ x'_n \end{bmatrix}$$

Thus, $x'_1$, $x'_2$, $x'_3$, etc. are vectors, each containing data from a different episode of spectral analysis. It is helpful to center the columns of the matrix X for later prediction modeling, as shown in Equation 2:

$$\overline{X} = X - \begin{bmatrix} 1 \\ 1 \\ 1 \\ 1 \\ 1 \\ \vdots \\ 1 \end{bmatrix} x'_m$$

where $x'_m$ is the mean value of the column, and $\overline{X}$ is the matrix containing vectors of centered values. The vector y will be made to contain the actual known glucose concentration of each spectra vector in X. It is also helpful for prediction to center this vector, as in Equation 3:

$$\overline{y} = y - y_m$$

At this step in the process of creating a prediction model, we need to make use of the DWT. Such DWT can be performed by a computer employing commercially available software, e.g., MATLAB (a matrix mathematics software sold by The MathWorks, Inc., 24 Prime Park Way, Natick, Mass. 01760). When performing any transform in spectral analysis, the basis functions of the chosen transform are selected to enable highlighting of the salient features of the spectra to be analyzed. In other words, at least some of the basis functions of the transform should be well matched with the important characteristics of the spectra. In the Discrete Wavelet Transform (DWT) used in this invention, there is large number of basis function sets that can be used. Thus, one of the important steps in the implementation of this invention is the selection of a wavelet basis that is appropriate for the specific analysis. The wavelets in the basis are by definition functions that meet certain mathematical criteria (see, Wavelets and Filter Banks, by Gilbert Strang and Truong Nguyen, Wellesley-Cambridge Press, 1996 ISBN: 0-9614088-7-1).

In analyzing the spectral information such as acquired in tissue spectroscopy, it is possible to choose a set of wavelet basis functions that contains some basis functions which closely resemble a spectral signature such as the absorption peak of the analyte to be measured. For example, some basis functions of the Daubechies D8 set are shaped substantially like the absorption peaks of pure glucose in the 4000–5000 wavenumbers range. Thus Daubechies D8 is one appropriate basis for implementing this invention when predicting glucose concentration. In one embodiment of this invention, a wavelet basis function set can be chosen since, to an observer, it visually appears to contain basis functions that suitably represent the important information in the spectra being studied. Thus, the wavelet basis functions are selected to correspond to the frequency and spatial characteristics of the spectral data.

In another embodiment of this invention a systematic optimization technique may be employed to test several sets of basis functions and choose one that optimizes a certain criterion, such as best correlation of one of the basis functions with the analyte signal or the least prediction error when the entire wavelet prediction method is performed in a reference data set (a calibration set). Once the optimal set of basis functions has been determined, a mathematical prediction model is built using this set of basis functions. This prediction model can then be used to determine the concentration of the analyte of interest from a single data set such as an absorption spectrum obtained from an unknown sample.

In addition to choosing the set of basis functions to be used in a DWT, the lowest resolution level of basis functions is also chosen to use in the DWT. We usually choose resolution level 2 as the lowest resolution level. A lower resolution level should be chosen, however, if the shape of the basis functions in these lower levels will match up well with the shape of the analyte of interest.

Once we have chosen a set of wavelet basis functions and the lowest resolution level, a matrix W will be created. The columns of W contain the basis vectors of the wavelet transform that is being used, as in Equation 4:

$$W = [\phi_1 \phi_2 \ldots \phi_n]$$

The matrix representation of the wavelet transform of the spectra in X will be called T. The rows of T are equal to the DWTs of the spectra vectors (rows) of $\overline{X}$, as in Equation 5:

$$T=\overline{X}W$$

By transforming our spectral data into this new wavelet domain, we should have concentrated information relevant to analyte concentration into as few variables as possible. At this stage a lot of the data in T would have low correlation with analyte concentration. This uncorrelated data should be eliminated from this process of building a prediction model since it represents nothing more than noise. Thus, the transformed spectra in T are truncated so that they contain only those resolution levels which are expected to contain information (characteristic frequencies of the analyte) relevant to predicting the analyte of interest. In addition, the spectra in T must often be truncated in order to perform some of the later steps of this process. Indeed, enough variables must always be eliminated from the spectra in T so that there are more rows than there are columns.

Choosing which resolution levels of T to use in the prediction process can be done in several ways. One way is to choose them based on the magnitude of the Fourier transforms. As mentioned earlier, all basis functions in a resolution level have the same magnitude of Fourier transforms. In order for a resolution level to be well suited for representing a particular analyte, the magnitude of Fourier transform of the resolution level should match up well with the magnitude of Fourier transform of the analyte's pure spectrum. In other words, the Fourier transforms of the selected basis functions of the selected resolutions levels will have peaks in the frequency ranges similar to the Fourier transform of the spectral data of the analyte of interest. This selection of resolution levels can be accomplished by inspecting the curves of the resolution levels of the basis functions and their Fourier transforms and selecting the ones with the wave number range of interest.

Figure 12:
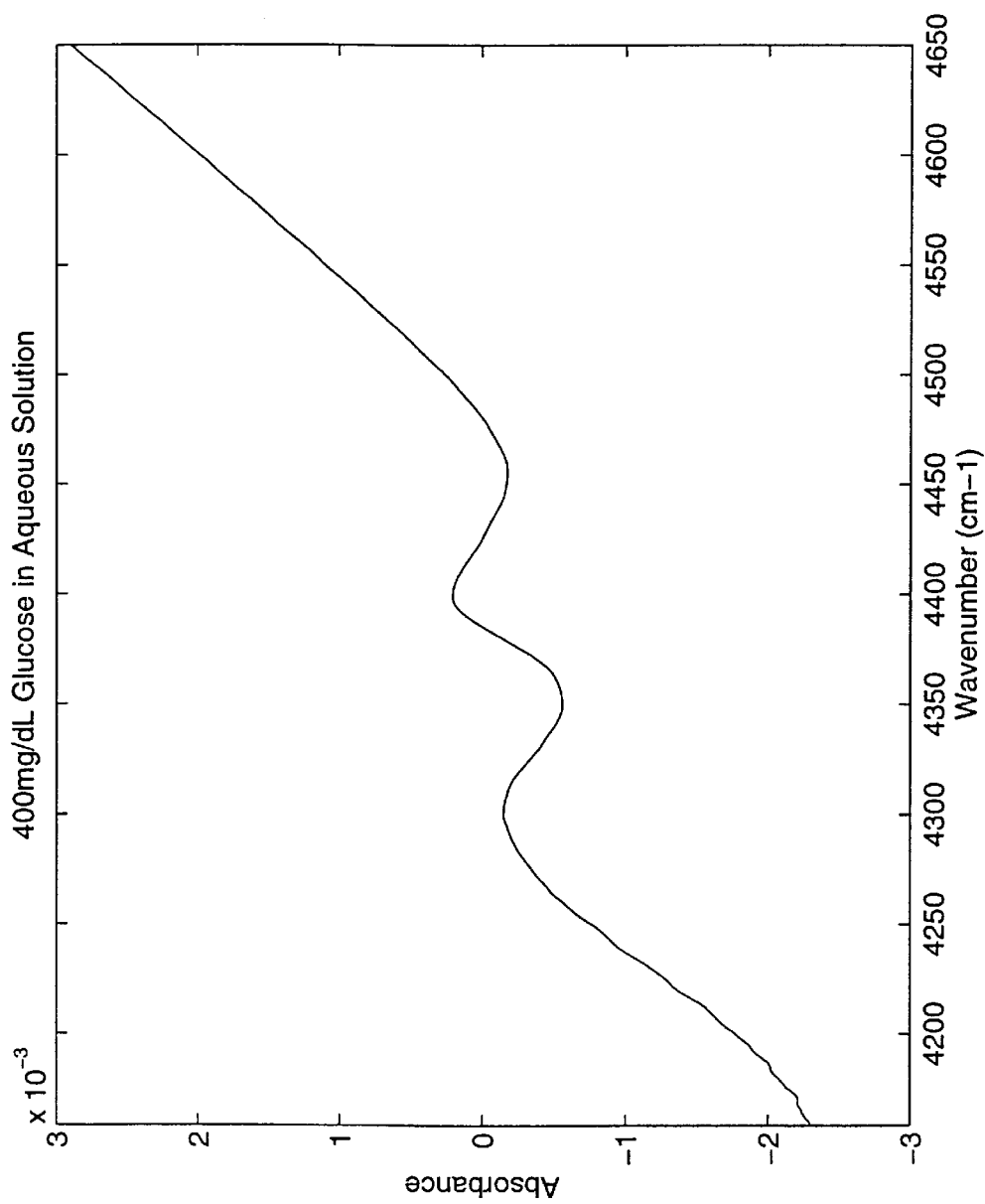
FIG. 12 shows an example of an absorbance spectrum of glucose in solution.
Figure 13:
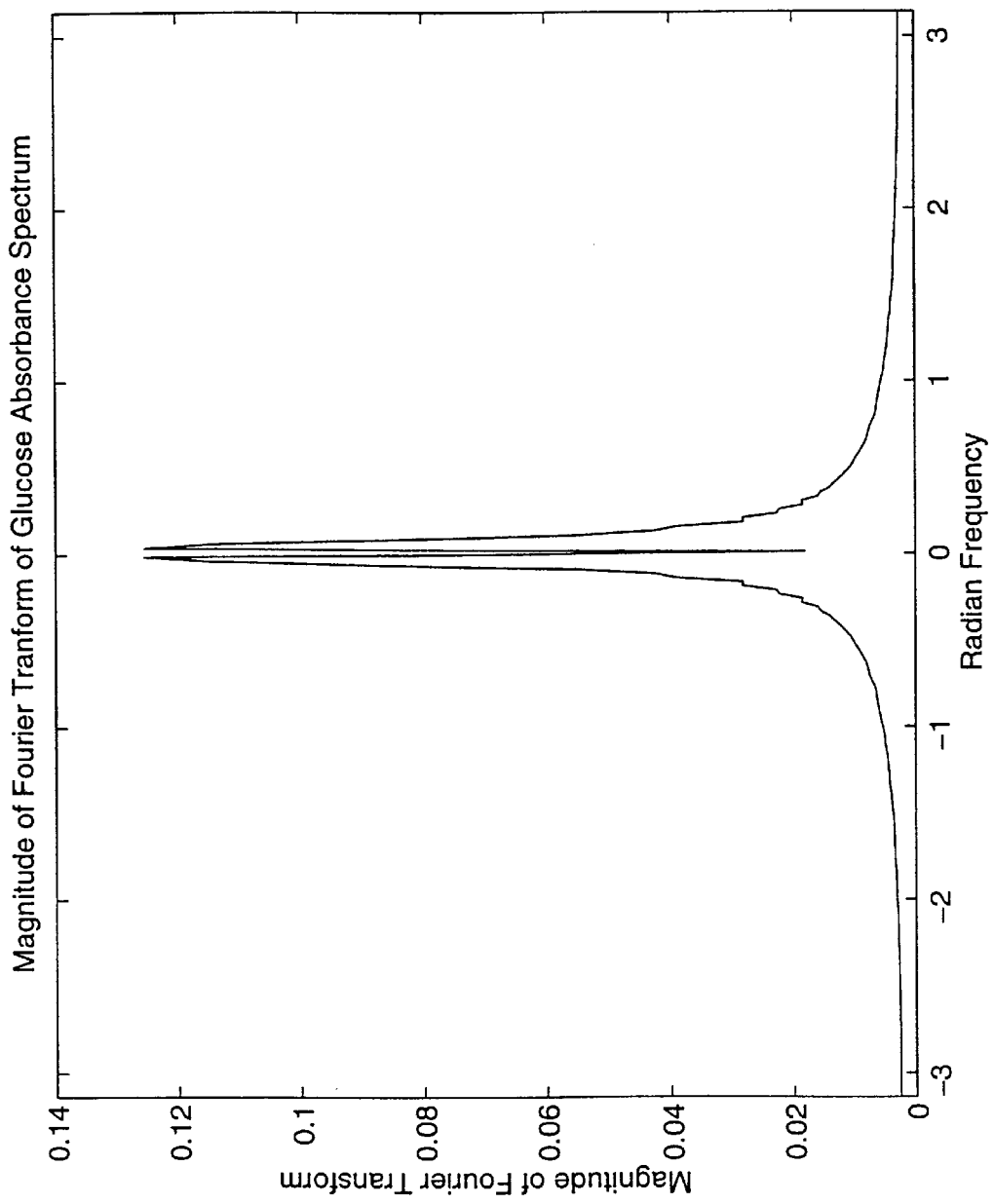
FIG. 13 shows an example of the Fourier transform of the spectrum of FIG. 12.

For example, FIG. 12 shows a 256 point absorbance spectrum obtained from 400 mg/dL glucose in an aqueous solution. FIG. 13 shows the magnitude Fourier transform of this spectra. When FIG. 13 is compared to the plots in FIG. 2, it should be apparent that some of the resolution levels of the DWT represented by FIG. 2 will contain very little information relevant to glucose concentration. For example, resolution levels seven, six, and five, represented by FIGS. 2a, 2b, and 2c, have very little in common with the plot in FIG. 13. On the other hand, resolution levels three and four, represented by FIGS. 2d, 2e, and 2f contain regions in their magnitude of Fourier transforms that overlap with the important features of the plot in FIG. 13. Thus, resolution levels three and four would likely be good resolution levels to include in the process of building a prediction model for this data.

Alternatively, an algorithm can be created to select the proper resolution levels using a quantitative optimization technique. Such optimization technique is also within the skill of one skilled in the art. Such algorithms can be run on computers. The optimization technique would use several different ranges of resolution levels in the prediction process that is presently being described. The range that optimizes a certain criterion, such as the least prediction error when cross validation is performed in a reference data set (a calibration set), could then be chosen as the best range of resolution levels.

Once the resolution levels for use in this process are chosen, the matrix T can be truncated so that it only contains spectra with these resolution levels. This new matrix will be called $T_a$, where the "a" represents the resolution level or levels of T that are included in $T_a$. $T_a$ can be found directly from by $\overline{X}$ using the formula $T_a = \overline{X} W_a$, where $W_a$ is derived from W and contains only the basis vectors in the applicable resolution level(s). For example, $T_3$ represents the matrix with rows containing resolution level 3 of the DWTs of the spectra vectors in $\overline{X}$.

The projection (q) of y onto the columns of $T_a$ is given by the following, Equation 6:

$$q=(T'_a T_a)^{-1} T'_a \overline{y}$$

This q is the regression vector that would be used in a regression equation between the variables in $T_a$ and predicted glucose concentration. Now that q is found, the final form of the prediction model can be obtained. This prediction model will give predicted analyte concentration ($y_{pred}$) of an unknown sample from its spectrum $x'_p$ as shown here in Equation 7:

$$y_{pred}=b_o+x'_p b$$

where $$b=V_a q; \; b_{o-ym}-x'_m b$$

with $y_m$ and $x'_m$ as defined in Equations (2) and (3).

In this application a wavelet basis function is chosen to be better matched to represent the spectral signal generated by the analyte species we are trying to analyze (for example, the absorption spectrum of glucose in solution). It is obvious that the shape of the absorption peaks of the analyte such as glucose are quite different from sine or cosine functions. Therefore, Fourier representation of this signal would be poor. However, Wavelet basis functions, due to their characteristics in resembling discontinuity and sharp peaks, are better suited to match the shape of the signal from the analyte to be analyzed and therefore will be better for analysis of the analyte.

Another advantage of wavelet transforms is that the individual wavelet basis functions are localized in space whereas Fourier sine and cosine functions are not. Thus, a very sharp signal from one analyte species can be represented by a high frequency wavelet basis function localized to the data space around the signal (e.g., absorption peak) for that species. While a wide peak generated by another species also present in the sample can be represented by a low frequency basis function over a wider data space. This property of wavelet transforms permits simpler isolation of sharp glucose peaks from a spectrum containing wide peaks generated by water and other interfering species.

Example of Modeling

The following is an illustrative example of how a model is developed for detecting quantitatively glucose concentration in aqueous solution. It is to be understood that other samples, i.e., solids, liquids in bottles, etc., can be analyzed by one skilled in the art employing a similar technique applying radiation and wavelet transform. Briefly stated, the method involves deriving a model of spectral data in relation to quantitative information (e.g., concentration) of an analyte using wavelet basis functions and matching the model with spectral data of a sample suspected to have the analyte, to find the quantitative information on the analyte in the sample.

To provide the spectra in this example, 42 aqueous solutions of glucose were irradiated and the resulting radiation interaction detected. The absorbance spectra were obtained using a BOMEM Michelson MB-155 FTIR (Bomem, Inc., 450 ave St-Jean-Baptiste, Quebec, PQ Canada G2E 5S5). Each individual spectrum contained 3,113 points of data and covered the wavenumber range 10,000 cm$^{-1}$–4000 cm$^{-1}$. These spectra were collected from sample solutions containing protein concentrations ranging from 40 g/L–60 g/L, glucose concentrations ranging from 20–400 mg/dL, and temperatures ranging from 34–40 degrees Celsius.

All forty-two (42) of the 3,113-point spectra were then transferred in their entirety into MATLAB. In MATLAB all of the spectra were truncated in the following manner. First, the index of the 3,113-point absorbance spectra corresponding to 4400 cm$^{-1}$ (or the closest wavenumber to 4400 cm$^{-1}$) was found. Then, the spectra were truncated 127 points from 4400 cm$^{-1}$ in the direction of the 4000 cm$^{-1}$ end, and 128 points from 4400 cm$^{-1}$ in the direction of the 10,000 cm$^{-1}$ end. This truncation process yields 256-point spectra (i.e., each having 256 point) covering the wavenumber range 4646 cm$^{-1}$–4100 cm$^{-1}$. The 256-point spectra, treated as vectors in MATLAB, were put into the columns of the matrix $X_{cal}$. The spectra in $X_{cal}$ are plotted in FIG. 3.

Then, a column concentration vector, $y_{cal}$, was created. As stated above, the entries of $y_{cal}$ corresponded to the glucose concentration of the solutions from which the columns (spectra) $X_{cal}$ were collected.

Next, a set of wavelet basis functions was chosen for later use in a discrete wavelet transform (DWT). In this illustrative case, the D8 (Daubechies-8) set of basis functions was chosen. The lowest resolution level of the DWT was also chosen at this point. In this example, the lowest resolutions level of the DWT was chosen to be resolution level 2.

Figure 4:
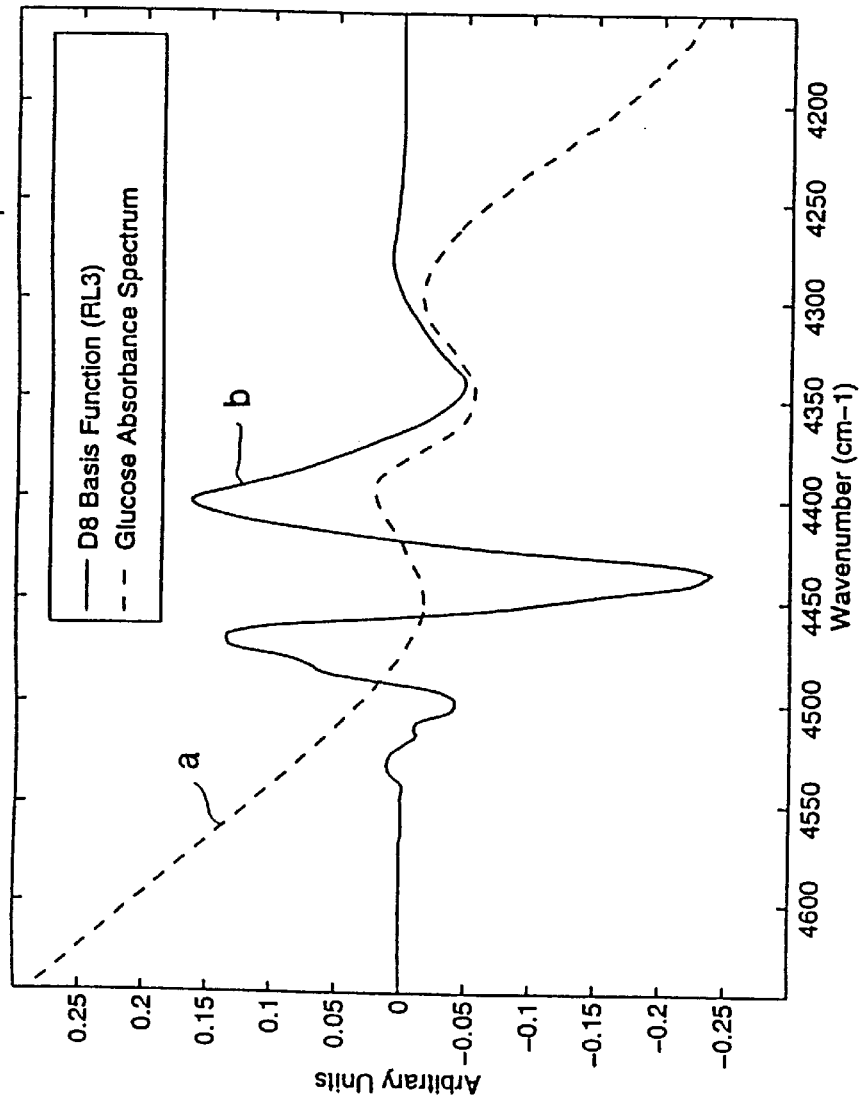
FIG. 4 and FIG. 5 show two examples of matching a DWT basis function to a glucose absorbance spectrum.
Figure 5:
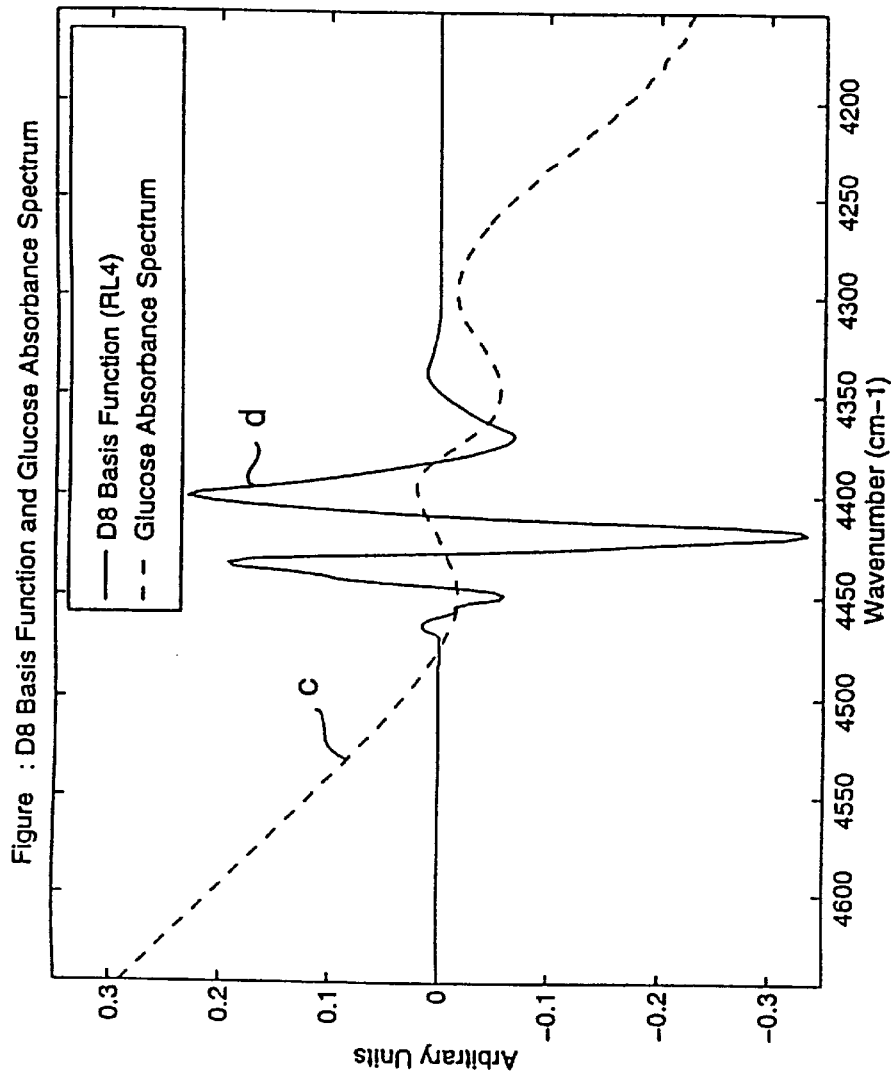

FIGS. 4 and 5 display two different basis functions of the D8 (from resolution levels 3 and 4) basis on the same set of axes as a magnified (100×) absorbance spectrum collected from a sample containing 400 mg/dL glucose and no protein at 37 degrees Celsius. In FIG. 4, the dotted line, a, is the resolution level 3 basis function and the solid line, b, represents the spectrum. In FIG. 5, the dotted line, c, is the level 4 basis function and the solid line, d, represents the spectrum. As can clearly be seen from both figures, the primary peaks of the basis functions match up well with the primary glucose absorbance peak at 4400 cm$^{-1}$. The basis function in FIG. 4 also seems to have a small peak at about the same point as the secondary glucose absorbance peak at 4300 cm$^{-1}$. Thus, D8 appears to be a good choice of wavelet basis.

At this point, a matrix W was created from the basis functions selected. The columns of W were the 256 (two hundred and fifty six) 256-point D8 wavelet basis functions. Thus, W was a 256-by-256 matrix.

Since the full DWTs of the truncated absorbance spectra in the calibration set would only contain a few points with useful information for predicting glucose concentration, only those points that had a high chance of containing glucose information were used in the final prediction formula. In this example, resolution levels 2h–4 (the high-frequency section of resolution level 2, resolution level 3, and resolution level 4) because these resolution levels of the D8 DWT contain the frequency ranges over which protein and glucose peaks are known to occur for the given wavenumber range. By selecting the resolution levels, the size of the matrix W is reduced, yielding a matrix $W_{2h-4}$ with a size of 256×28 described above in Equations 1 to 7. This matrix is constrained to always have fewer columns than the number of spectra in the calibration set. $W_{2h-4}$ had 28 columns, which is indeed less than the 42 spectra in the calibration set.

As per the method described above in Equations 1 to 7, the calibration data matrix $X_{cal}$ is centered for each wave number by finding the difference of the truncated spectral data from the average, via the following operation, similar to Equation 2 above, using the transpose X'cal of $X_{cal}$, as shown in the following Equation 8:

$$\overline{X}'_{cal} = X'_{cal} - \begin{bmatrix} 1 \\ 1 \\ 1 \\ \vdots \\ 1 \end{bmatrix} \overline{x}'$$

where the $\overline{x}'$ vector is the mean of the transpose spectral data $X'_{cal}$ of the 42 spectra. Further, the concentration data of the calibration samples from which the spectra were derived are put into vector form, $y_{cal}$. The entries of this $y_{cal}$ matrix correspond to the concentrations of the analyte from the columns (i.e., spectra) of the $X_{cal}$ matrix. The $y_{cal}$ is also centered, similar to Equation 3 above, by finding the difference of the concentration data from the average, as in the following Equation 9:

$$\overline{y}_{cal} = y_{cal} - \overline{y}$$

where $\overline{y}$ is the mean of the concentration of the 42 samples.

Subsequently, $\overline{X}_{cal}$ (or rather $\overline{X}'_{cal}$) and $W_{2h-4}$ were used to produce a new matrix, the resolution matrix T, as shown in Equation 10:

$$T = \overline{X}'_{cal} W_{2h-4}$$

T was a 42 by 28 matrix. The rows of T contained resolution levels 2h–4 of the DWTs of the columns (spectra) of $\overline{X}_{cal}$.

Next, the prediction coefficient vector b was found using the Equation 11:

$$b = W_{2h-4}(T'T)^{-1}T'\overline{y}_{cal}$$

The scalar offset coefficient $b_o$ for the prediction model was obtained by finding the dot product of the regression coefficients b obtained above and the average spectrum vector and then subtracting this dot product from the mean concentration of the analyte in the calibration samples, as shown in the following Equation 12:

$$b_o = \overline{y} - \overline{x}'b$$

Figure 6:
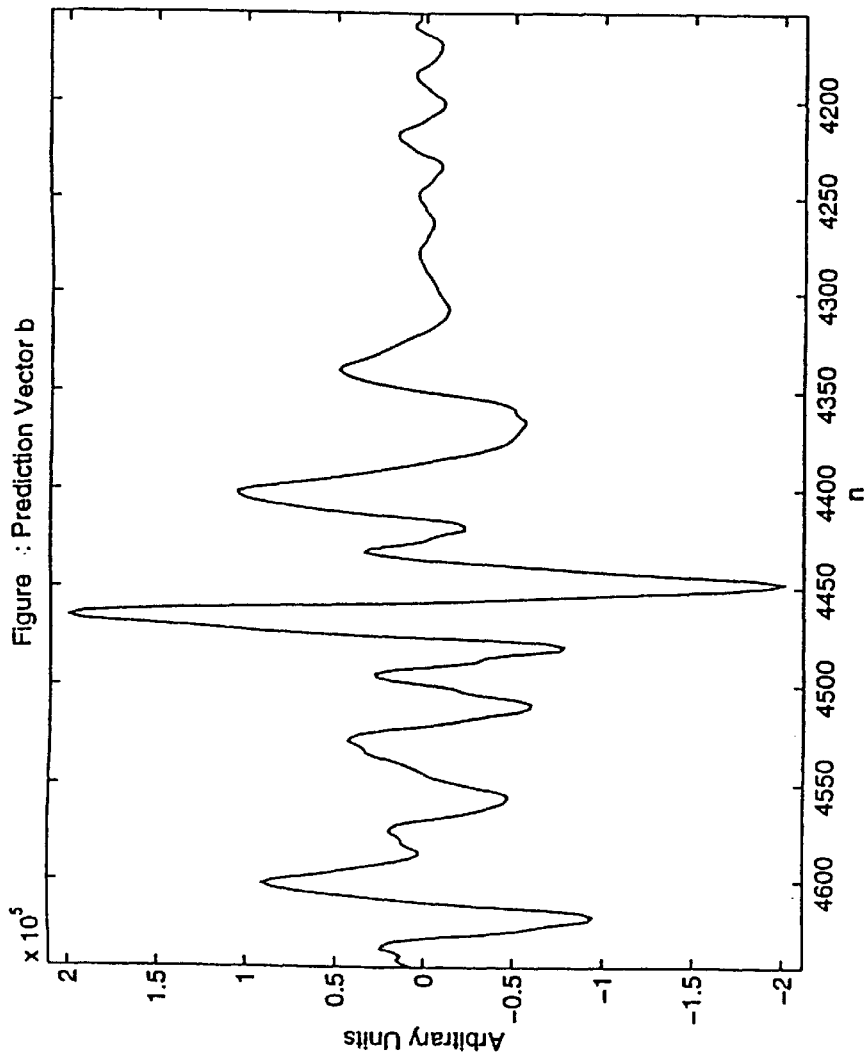
FIG. 6 shows a prediction vector b in a prediction model according to the present invention.
Figure 7:
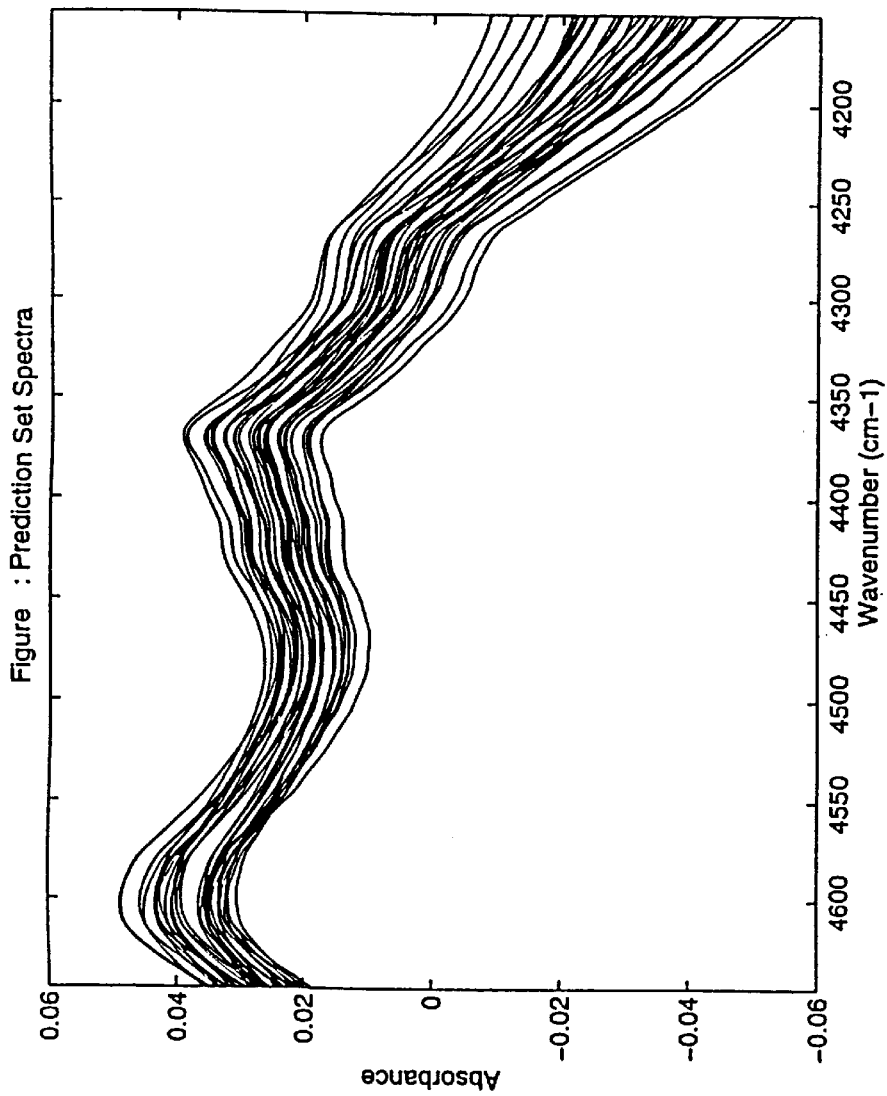
FIG. 7 shows a set of spectra of sample the glucose concentrations of which are to be determined.

FIG. 6 shows the prediction vector b, plotted against the corresponding wavenumbers of the signals that will later be dotted with b.

Determination of Quantitative Information Using the Model

When a sample is suspected to contain the analyte of interest, the sample can be irradiated with the radiation to obtain a spectrum as with the n calibration samples described in the above. As previously stated, a part of a human body can be considered a sample herein.

In this illustrative example, forty-two (42) NIR absorbance spectra were obtained using a BOMEM Michelson MB-155 FTIR spectrometer in the same manner as described in the above model. Each individual spectrum contained 3,113 points and covered the wavenumber range 10,000 cm$^{-1}$–4000 cm$^{-1}$. These spectra were collected from prediction sample solutions containing protein concentrations ranging from 40 g/L–60 g/L, glucose concentrations ranging from 20–400 mg/dL, and temperatures ranging from 34–40 degrees Celsius. None of these spectra in the prediction set, however, contained the same protein and glucose concentrations as any spectrum in the calibration set.

All forty-two (42) 3,113-point spectra were then transferred in their entirety into MATLAB. In MATLAB all of the spectra were truncated in the same manner as described in the above Model. Then, the forty-two 256-point spectra were put into the columns of a matrix called $X_{pred}$. The spectra in $X_{pred}$ are plotted in FIG. 5.

Figure 8:
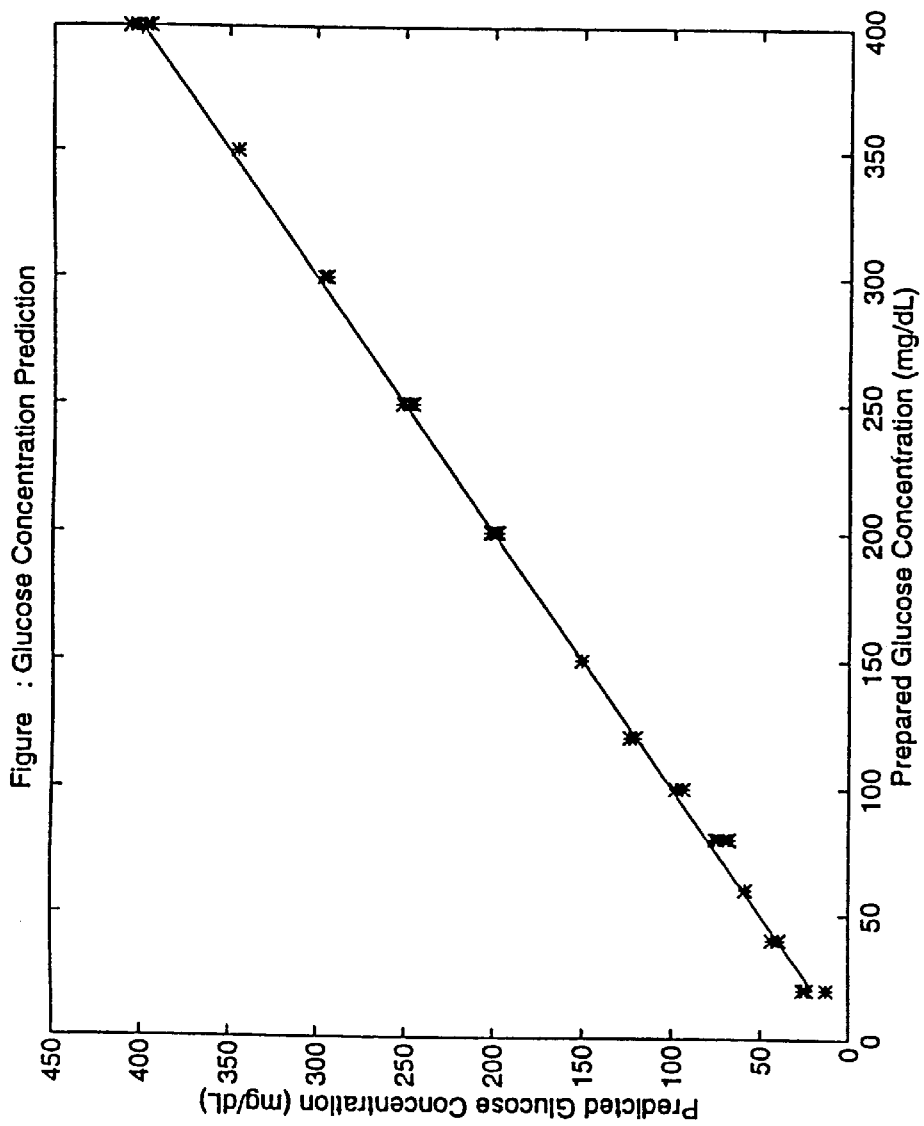
FIG. 8 shows the comparison of the predicted result and the known value of glucose solution samples, predicted according to the technique of the present invention.

Prediction was then performed using $b_o$ and b found in the model developed above and Equation 13:

$$\bar{y}_{pred} = b_o + X'_{pred} b$$

where $\bar{y}_{pred}$ contained the predicted glucose concentration of each spectrum in $X_{pred}$ and $X'_{pred}$ is the transpose of $X_{pred}$. FIG. 8 shows the plot of predicted versus actual glucose concentration. The results show that the predicted values represent the actual concentrations very well.

In this way, the model can be used to predict quantitative information of the analyte of interest in unknown samples. It is to be understood that one skilled in the art will be able to made obvious modifications, and such modification are within the scope of the present invention. For example, the mathematics can be reformulated using equivalent mathematics, curve fitting methods other than linear regression can be used, and the order or extent of the truncation steps may be modified. Further, although we use concentration as the quantitative information as the example in the above description, other quantitative information such as mass, mole, and the like, can be used, if the volume, mass, etc., of the sample is known.

Figure 9:
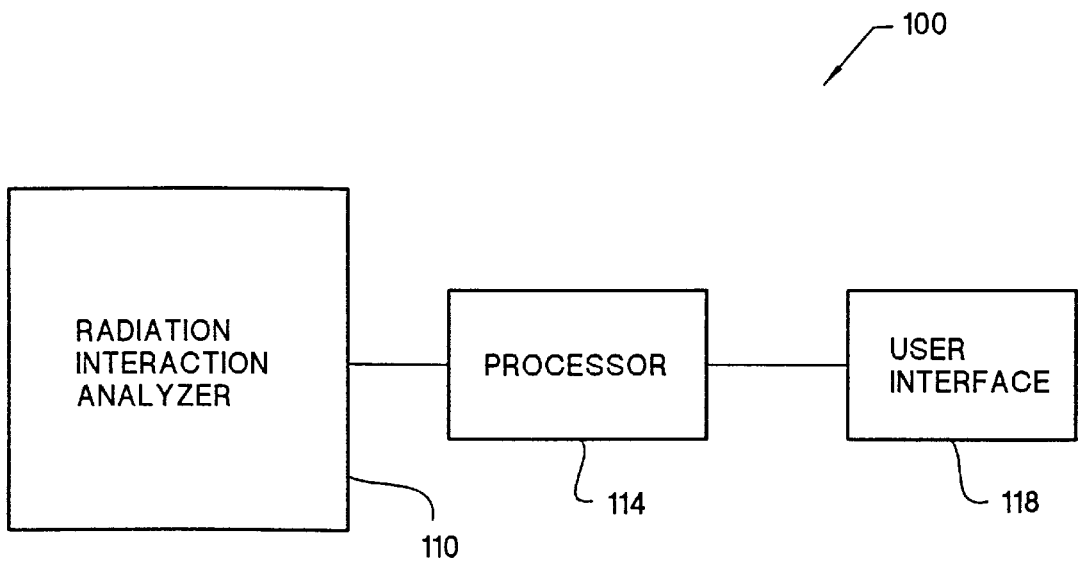
FIG. 9 shows an apparatus according to the present invention.
Figure 10:
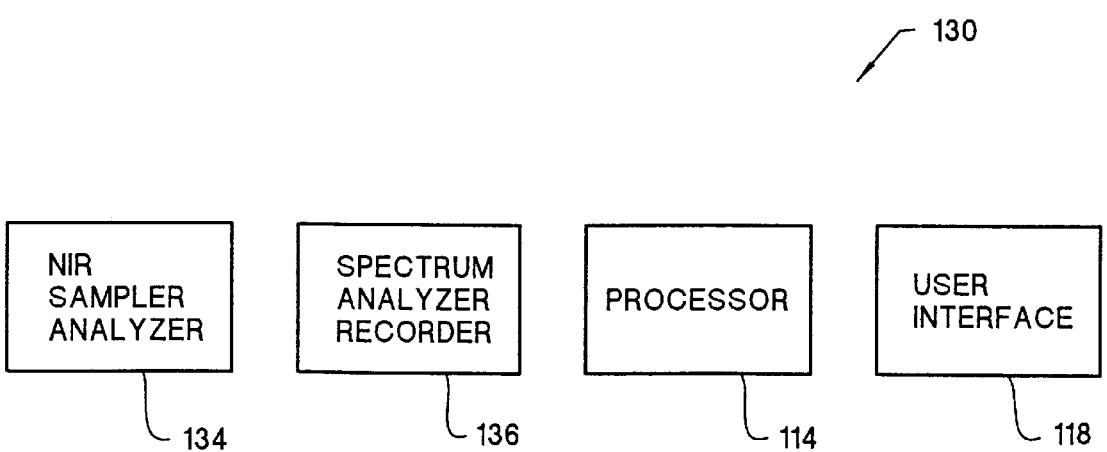
FIG. 10 shows a more specific apparatus according to the present invention.
Figure 11:
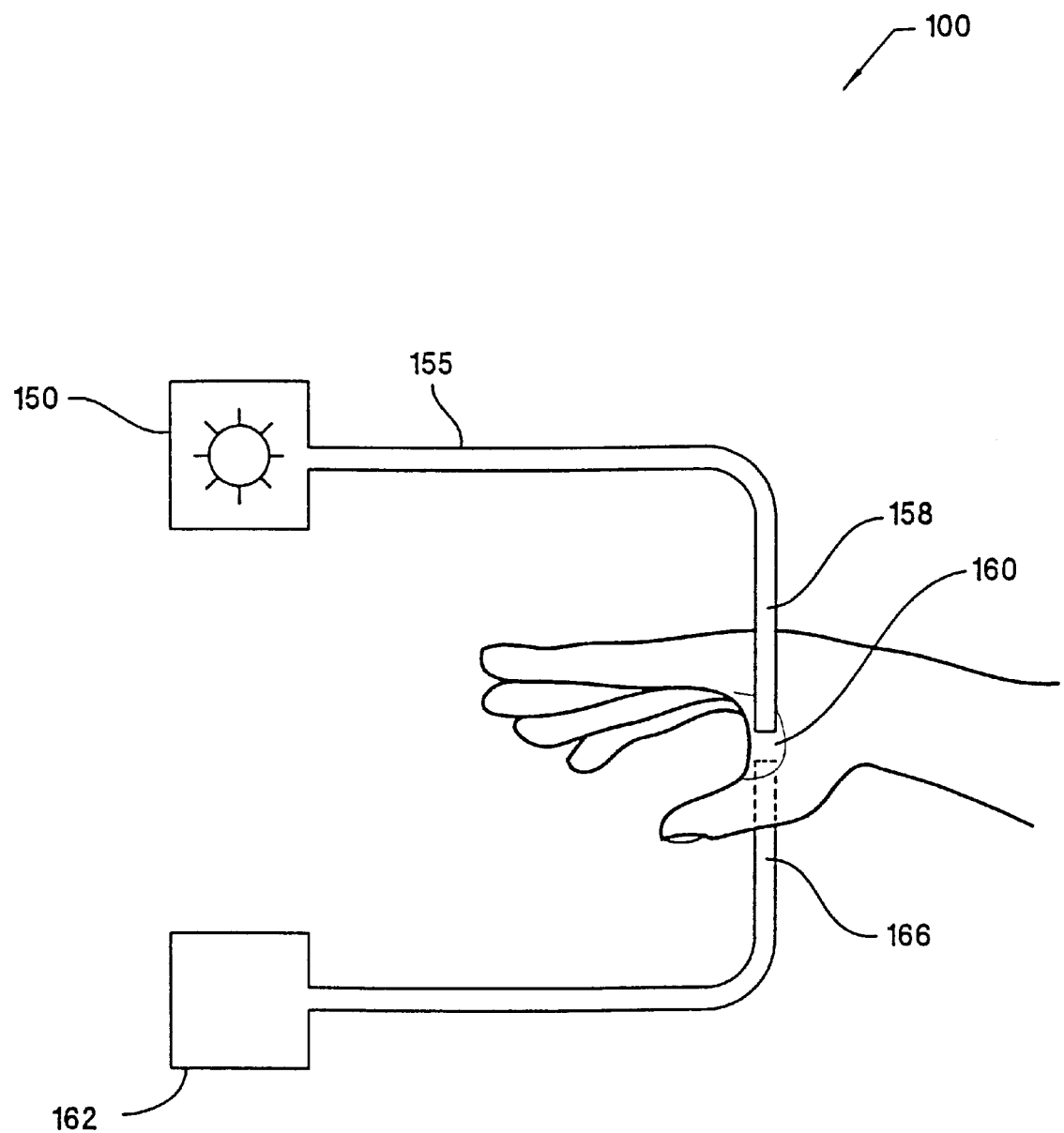
FIG. 11 shows an embodiment of an apparatus for radiating a part of a hand and sensing the electromagnetic radiation interaction.

The apparatus used in the present invention can be composed of standard commercial units of electromagnetic energy radiation equipment detectors, computers, monitors, amplifiers, and the like. FIG. 9 shows an embodiment of an apparatus that can be used for determining the concentration of an analyte in solution according to the present invention. The apparatus 100 includes an analyzer 110 by radiation interaction of the analyte in solution. The data of the electromagnetic wave interaction, such as absorbance, transmission, light scattering, etc. are analyzed in a processor 114 to obtain the spectra of the electromagnetic wave interaction data. The processor 114 further can determine the basis functions. Alternatively, a person can manually select the basis functions. The processor can, based on the basis functions selected, predict the concentration of the analyte according to an algorithm embodying the DWT technique described above. The result of the analysis can be communicated to the user by a user interface, such as a display, or to another analytical or computing device in remote site. In a more specific embodiment the electromagnetic wave interaction analyzer is a near infra-red (NIR) absorbance spectrometer 134. In the NIR absorbance spectrometer, light of specific wavelength is imparted on the sample and the absorbance analyzed to obtain data with the absorption peaks. The NIR absorbance spectrometer or the spectrum analyzer can analyze the spectral data. The processor can be a computer, microprocessors, etc. known in the art. The user interface for displaying the analytical results can be a CRT monitor, printer, plotter, or the like. Alternatively, the data, the algorithm, and the results can be stored separately or together in a storage medium such as a computer, hard disk, floppy disk, tape, IC, and the like, for later use. As an alternative to NIR, as described above, radio frequency interaction can be used. In this case, a radio frequency radiation generator and sensor for sensing the radio frequency interaction will be used. Devices for non-invasively irradiating a part of the body to obtain electromagnetic wave interaction for spectral analysis are known in the art. For example, NIR absorption using fiber optics for directing light to the webbing between the thumb and the forefinger is disclosed by Small et al., International Patent Application No. WO 95/22046, which description of the technique for detection of physiological chemical is incorporated by reference herein). As previously stated, devices for utilizing radio frequency for determining chemical in a human body are disclosed by Fuller, et al. (supra). In the present invention, electromagnetic radiation can be directed to, e.g., as shown in FIG. 11, the webbing between the thumb and the forefinger, the earlobe for electromagnetic interaction such as NIR, far IR absorption, and radio frequency radiation. In FIG. 11, the NIR light is generated by a NIR light source 150 such as a halogen lamp. The NIR light is transmitted through an optical cable 115 to light exit end 158 to the webbing 160. Light transmitted through the webbing 160 is carried by another optical fiber 164 to a detector 166 to be detected and later analyzed for spectral characteristics.

Although the preferred embodiment of the present invention has been described and illustrated in detail, it is to be understood that a person skilled in the art can make modifications within the scope of the invention. For example, the present technique can be used to measure chemical concentration in samples of solid, liquid, non-physiological fluids as long as electromagnetic interaction can be used to obtain spectra. Further, based on the present disclosure, the use of algorithms for wavelet analysis would be simple and obvious to one skilled in the art of wavelet analysis. For example, rather than using the basis functions of the DWT, one could also use the basis functions of a discrete wavelet packet transform. The basis functions of a wavelet packet transform are divided into resolution level detail and resolution vectors. In using wavelet packet transform, one would simply choose the sets of basis functions to use in creating the prediction equation in the same manner as described here for choosing resolution levels.

What is claimed is:

1. An apparatus for analyzing analyte composition of a sample without immersing a part of the apparatus therein, comprising:
   (a) a source of electromagnetic radiation for irradiating the sample to result in radiation interaction;
   (b) a detector for detecting electromagnetic radiation resulting from the radiation interaction from the sample to result in analytical data, said detected electromagnetic radiation having a signal indicative of the analyte; and
   (c) a processor having a modeling algorithm for applying to said analytical data from step (b) to determine quantitative characteristics of the analyte in the sample, said modeling algorithm having parameters, for determining said quantitative characteristics, obtained by applying wavelet basis functions of resolution levels having amplitude-frequency characteristics resembling amplitude-frequency characteristics of radiation interaction data derived by irradiating calibration samples having known concentration of the analyte.

2. An apparatus according to claim 1 wherein the modeling algorithm applies said wavelet basis functions to calibration data obtained from the detector over a spectrum of frequencies to derive parameters of prediction equations for analyte concentration.

3. An apparatus according to claim 1 wherein the modeling algorithm applies said wavelet basis functions of resolution levels over a selected portion of a spectrum of frequencies of the electromagnetic radiation irradiating the sample for matching characteristic frequencies of the analyte.

4. An apparatus according to claim 1 wherein the radiation source emits light of frequencies that penetrates non-invasively a physiological body surface to irradiate tissue underneath the body surface.

5. An apparatus according to claim 1 wherein the processor derives the parameters from wavelet basis functions of the Daubechies set to correspond to the frequency and amplitude characteristics of the radiation interaction of glucose as the analyte.

6. A method for detecting quantitatively an analyte in a sample, comprising:
   (a) irradiating electromagnetic radiation on the sample to result in radiation interaction;
   (b) detecting electromagnetic radiation resulting from the radiation interaction from the sample to result in data, said detected electromagnetic radiation having a signal indicative of the analyte; and
   (c) applying to the data from step (b) a modeling algorithm to determine quantitative characteristics of the analyte in the sample, said model algorithm having parameters for determining said quantitative characteristics, obtained by applying wavelet basis functions of resolution levels having amplitude frequency characteristics resembling amplitude-frequency characteristics of radiation interaction data derived by irradiating calibration samples having known concentration of the analyte.

7. A method according to claim 6, further comprising irradiating calibration samples and applying wavelet basis functions to calibration data derived from the irradiation over a spectrum of frequencies of the calibration samples to derive the parameters.

8. A method according to claim 7, further comprising selecting wavelet basis functions having prominent features over a selected portion of a spectrum of frequencies of the electromagnetic radiation irradiating the sample corresponding to frequency and spatial characteristics of the radiation interaction of the analyte.

9. A method according to claim 7, further comprising selecting wavelet basis functions and resolution levels thereof having prominent peaks over a spectrum of frequencies resembling frequency and spatial characteristics of the radiation interaction of the analyte.

10. A method according to claim 7, comprising forming the modeling algorithm by deriving a regression model having a vectorial equation the constants of which are obtained by applying wavelet basis functions to calibration radiation interaction data over a spectrum of frequencies.

11. A method according to claim 10 wherein the regression model has the form of $y_{pred}=b_o+x'_i b$ where $y_{pred}$ is a vector of the predicted concentration, $b_o$ is a scalar constant and b is a vector of constants derived by applying wavelet basis functions, and where $x'_i$ is a vector of radiation interaction analytical data; $b_o$ and b being the parameters in the modeling algorithm.

12. A method according to claim 7, further comprising analyzing the spectra of the radiation interaction of the calibration sample to derive the calibration data and performing wavelet transform on the calibration data to obtain wavelet basis functions of the calibration data.

13. A method according to claim 7, wherein the step of irradiating calibration samples includes irradiating near infrared radiation and the method further comprises applying the wavelet basis functions by selecting Daubechies sets corresponding to frequency and amplitude characteristics of radiation interaction of glucose.

14. A method according to claim 13, wherein the Daubechies sets are selected based on wavelet basis function resolution levels having prominent features corresponding to frequency and amplitude characteristics of absorbance spectra of glucose.

15. A method according to claim 6, wherein step (a) comprises directing electromagnetic waves of frequencies that penetrate non-invasively a physiological body surface to irradiate tissue underneath the body surface to result in the radiation detected.

16. A method according to claim 6, further comprising truncating part of the data of step (b) to reduce noise before applying wavelet analysis.

17. A method according to claim 6, further comprising the step of irradiating a spectrum of electromagnetic radiation on multiple calibration samples to result in radiation interaction and detecting electromagnetic radiation resulting from the radiation interaction from the calibration samples to result in the calibration data for developing the modeling algorithm, said detected electromagnetic radiation having a signal indicative of the analyte in the calibration samples.

18. A method for non-invasively detecting quantitatively an analyte in a physiological fluid-containing sample from a patient, comprising:
   (a) irradiating electromagnetic radiation at a surface of the physiological sample to result in radiation interaction of the electromagnetic radiation with physiological fluid in the sample;
   (b) detecting electromagnetic radiation resulting from the radiation interaction from the sample to result in evaluation data, said detected electromagnetic radiation having a signal indicative of the analyte in the physiological fluid in the sample; and
   (c) applying a modeling algorithm to at least a portion of the evaluation data to determine the quantitative characteristics of the analyte in the physiological fluid based on the evaluation data, the modeling algorithm having been developed digitally by applying wavelet basis functions of resolution levels having amplitude-frequency characteristics resembling amplitude-frequency characteristics of calibration data of radiation interaction derived by shining electromagnetic radiation of a spectrum of frequencies on calibration samples having known concentration of the analyte.

19. A method according to claim 18, further comprising:
   (a) irradiating a spectrum of electromagnetic radiation on multiple calibration samples to result in radiation interaction and detecting electromagnetic radiation resulting from the radiation interaction from the calibration samples to result in the calibration data, said detected electromagnetic radiation having a signal indicative of the analyte in the calibration samples; and
   (b) digitally processing at least a portion of the calibration data in matrix form covering the multiple calibration samples under the spectrum using wavelet-basis-functions to derive the model algorithm of the radiation interaction of the analyte via selecting wavelet basis functions and resolution levels thereof having prominent peaks in the amplitude-frequency characteristics resembling amplitude-frequency characteristics of the radiation interaction of the analyte.

20. An article of manufacture comprising a program storage medium, tangibly embodying a program code means readable by a computer for causing the computer to analyze the concentration of an analyte in a sample, the program code means including:

(a) code means for digitally processing calibration data obtained from irradiation of a plurality of calibration samples with electromagnetic radiation of a spectrum of frequencies, said means for digitally processing applying wavelet basis functions of resolution levels having amplitude-frequency characteristics resembling the amplitude-frequency characteristics of the calibration data to derive a model algorithm of the radiation interaction of the calibration sample; and (b) code means for applying the modeling algorithm in matrix operation to the evaluation data obtained from radiating evaluation samples with electromagnetic radiation of a spectrum of frequencies, to determine the quantitative characteristics of the analyte in the evaluation sample based on the evaluation data.

\* \* \* \* \*